US012767924B2

(12) United States Patent
Jain et al.

(10) Patent No.: US 12,767,924 B2
(45) Date of Patent: Oct. 20, 2026

(54) FORMULATIONS OF MICROENCAPSULATED MICROBIAL CULTURE WITH HIGH STORAGE STABILITY

(71) Applicant: Chr. Hansen A/S, Hoersholm (DK)

(72) Inventors: Deepak Jain, Mumbai (IN); Surender Kumar Dhayal, Hoersholm (DK)

(73) Assignee: Chr. Hansen A/S, Hoersholm (DK)

( * ) Notice: Subject to any disclaimer, the term of this patent is extended or adjusted under 35 U.S.C. 154(b) by 637 days.

(21) Appl. No.: 18/264,954

(22) PCT Filed: Feb. 10, 2022

(86) PCT No.: PCT/EP2022/053254
§ 371 (c)(1),
(2) Date: Apr. 1, 2024

(87) PCT Pub. No.: WO2022/171744
PCT Pub. Date: Aug. 18, 2022

(65) Prior Publication Data

US 2024/0150706 A1 May 9, 2024

(30) Foreign Application Priority Data

Feb. 11, 2021 (EP) .................................... 21156596

(51) Int. Cl.
*C12N 1/04* (2006.01)
*C12N 1/205* (2026.01)
*C12N 11/04* (2006.01)
*C12R 1/225* (2006.01)

(52) U.S. Cl.
CPC ............... *C12N 1/205* (2021.05); *C12N 1/04* (2013.01); *C12N 11/04* (2013.01); *C12R 2001/225* (2021.05)

(58) Field of Classification Search
None
See application file for complete search history.

(56) References Cited

FOREIGN PATENT DOCUMENTS

| | | | | |
|---|---|---|---|---|
| CN | 105310080 A | 2/2016 | | |
| CN | 109700032 A | 5/2019 | | |
| CN | 111713685 A | 9/2020 | | |
| WO | WO-2014006261 A2 * | 1/2014 | .............. A61P 31/12 | |
| WO | WO-2014/082132 A1 | 6/2014 | | |
| WO | WO-2016/161506 A1 | 10/2016 | | |

OTHER PUBLICATIONS

Sbehat et al. "Microencapsulation of Probiotics for Food Functionalization: An Update on Literature Reviews" (Year: 2022).*
U.S. Appl. No. 18/042,579, filed Feb. 22, 2023.
Abd El-Salam; Mohamed H. et al.; "Preparation and properties of milk proteins-based encapsulated probiotics: a review"; Dairy Sci. & Technol., vol. 95, No. 4; Apr. 3, 2015; pp. 393-412.
Mogensen, G. et al.; "Inventory of Microorganisms with a Documented History of Use in Food"; Bulletin of the IDF, 377; 2002; pp. 10-19.
Oliveira, A.C. et al.; "Stability of microencapsulated *B. lactis* (Bl 01) and *L. acidophilus* (LAC 4) by complex coacervation followed by spray drying"; Journal of Microencapsulation 24(7); Nov. 2007; pp. 673-681.
Vandamme, Thierry F. et al.; "Chapter 5, Microencapsulation of probiotics"; Encapsulation and Controlled Release Technologies in Food Systems; 2016; pp. 97-128.
Zhao, Meng et al.; "Probiotic encapsulation in water-in-water emulsion via heteroprotein complex coacervation of type-A gelatin/sodium caseinate"; Food Hydrocolloids 105, 105790; Feb. 21, 2020; 8 pages.
Zheng, Jinshui et al.; "A taxonomic note on genus *Lactobacillus*: Description of 23 novel genera, emended description of the genus *Lactobacillus* Beijerinck 1901, and union of *Lactobacilliae* and *Leuconostocaceae*"; Int. J. Syst. Evol. Microbiol., vol. 70, No. 4; Apr. 2020; pp. 2782-2858.
Li et al., 2020, Food and Fermentation Sciences & Technology, 56, 6, 2-99—including EN abstract.
Oliveira et al., 2007, Journal of Microencapsulation, 24, 7, 685-693.
Zhao et al., 2018, Food & Function, 9, 1000-1008.

* cited by examiner

*Primary Examiner* — Susan T Tran
(74) *Attorney, Agent, or Firm* — Eric J. Fechter

(57) ABSTRACT

The present invention relates to microencapsulated microbial cultures with high storage stability and methods for producing these. In particular, the present invention relates to microbial cultures formulated at high ratios of encapsulation matrix material to core material.

12 Claims, 3 Drawing Sheets

FORMULATIONS OF MICROENCAPSULATED MICROBIAL CULTURE WITH HIGH STORAGE STABILITY

CROSS-REFERENCE TO RELATED APPLICATIONS

The present application is the U.S. National Stage of International Application No. PCT/EP2022/053254, filed Feb. 10, 2022, and claims priority to European Patent Application No. 21156596.5, filed Feb. 11, 2021.

TECHNICAL FIELD OF THE INVENTION

The present invention relates to microencapsulated microbial cultures with high storage stability and methods for producing these. In particular, the present invention relates to microbial cultures formulated at high ratios of encapsulation matrix material to core material.

BACKGROUND OF THE INVENTION

In human and animal bodies, microbial cultures, such as lactic acid bacteria (LAB), are the part of normal microbiota. LAB are mostly used as starter cultures in fermented dairy foods and beverages as they can help to improve the nutritional and organoleptic characteristics, as well as extend the shelf life. Some strains of LAB have been reported to exhibit health benefits to human and animals and may thereby be referred to as probiotic strains. The typical process for the production of LAB is through fermentation followed by concentration and freezing of cell biomass. When it comes to applications of LAB, dried powder form produced using freeze drying (FD) is often desired. The dried powders are frequently kept for extended periods of time before utilized in a final application.

Microbial cultures, such as LAB, are very sensitive to environmental stresses applied during freezing and FD, causing the addition of cryo/lyo protectants to be necessary for protecting and retaining viability during processing. Moreover, it is well-known that storage of microbial cultures, such as LAB, at ambient (25-35° C.) or higher temperature adversely affect the viability of the microbial cultures. Therefore, storage for extended periods of time necessitates expensive cooling facilitates that are not always available at the point of use.

While there are several concepts on cryo/lyo protectants to shield the LAB during freezing and FD, all these protectants (ingredients) have limited impact on the storage stability. Therefore, there is an unmet need for methods of protecting microbial cultures during freezing and FD and which at the same time enhance the storage stability of these dried microbial cultures.

Hence, it would be advantageous to provide an improved method for preparing dried microbial cultures that maintain viability after freezing or freeze drying and over extended periods of storage even at elevated temperatures. Specifically, such methods and dry microbial cultures per se may be advantageous in the preparation of products which are exposed to conditions of increased environmental stress.

SUMMARY OF THE INVENTION

The present invention relates to a microencapsulation approach wherein microbial cultures are formulated at high ratios of encapsulation matrix material to core dry matter and selecting a coacervate-forming encapsulation matrix which efficiently shield the entrapped microbial culture. In particular, the present invention discloses methods for producing microencapsulated microbial cultures that endure dry processing and exhibit enhanced storage stability upon storage at even 37° C. for extended periods of time. The obtained microencapsulated microbial cultures are well suited for applications in which storage at depressed temperatures is not feasible.

Thus, an object of the present invention relates to the provision of methods for preparing a microbial culture that may be utilized under conditions independent of refrigerated storage.

In particular, it is an object of the present invention to provide an improved method for production of dry microbial cultures that retain cell viability after dry processing and storage at elevated temperatures.

Thus, an aspect of the present invention relates to a microencapsulated microbial culture, wherein said microbial culture is entrapped in a coacervate comprising:

i) a core material comprising a microbial culture, and
ii) an encapsulation matrix comprising one or more matrix components, wherein the ratio (wt %/wt %) of encapsulation matrix to core material is at least 2.

Another aspect of the present invention relates to a composition comprising the microencapsulated microbial culture as described herein.

A further aspect of the present invention relates to a product comprising the microencapsulated microbial culture or the composition as described herein, wherein the product is selected from the group consisting of a feed, a plant health product, a food, a beverage and a pharmaceutical product.

An even further aspect of the present invention relates to a method for preparing a microencapsulated microbial culture or a composition as described herein, said method comprising the steps of:

i) mixing a microbial culture with a first matrix comprising one or more first matrix components to form a first mixture, and
ii) mixing the first mixture with a second matrix comprising one or more second matrix components to form a microencapsulated microbial culture, wherein said one or more first matrix components and said one or more second matrix components are not the same.

Yet another aspect of the present invention relates to a microencapsulated microbial culture or a composition obtainable by a method as described herein.

Still another aspect of the present invention relates to use of a microencapsulated microbial culture or a composition as described herein in a product selected from the group consisting of a feed, a plant health product, a food, a beverage and a pharmaceutical product.

Figure 1:
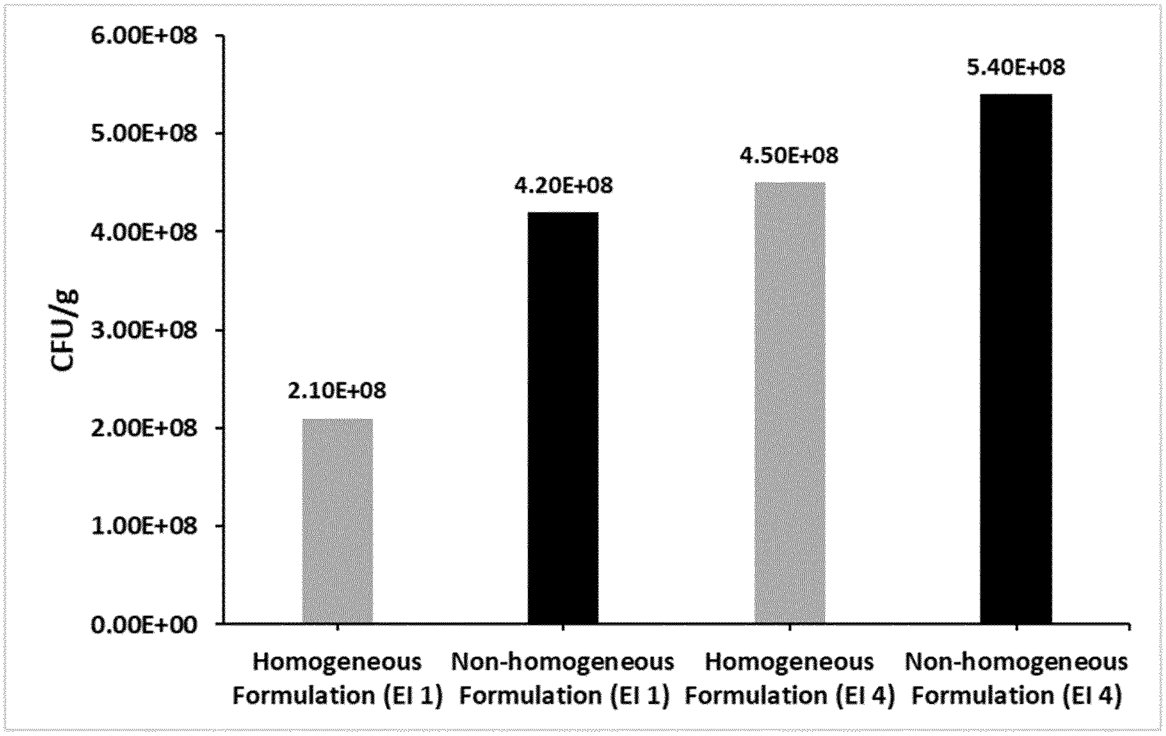
FIG. 1 shows initial CFU/g of homogeneous and non-homogeneous formulations, respectively, diluted in $CaCO_3$ at EI 1 or 4.

The present invention will in the following be described in more detail.

DETAILED DESCRIPTION OF THE INVENTION

Definitions

Prior to outlining the present invention in more details, a set of terms and conventions is first defined:

Core Material

In the present context, the term "core material" refers to a preparation comprising a microbial culture. Preferably, the microbial culture is provided as a liquid cell concentrate.

Microbial Culture

In the present context, the term "microbial culture" refers to a population of microorganisms. Microorganisms include all unicellular organisms, such as archaea and bacteria, but also many multicellular organisms, such as fungi and algae. Microbial cultures as referred to herein does not include unwanted microorganisms that contribute to spoilage or risk of disease.

Probiotic Culture

In the present context, the terms "probiotic" or "probiotic culture" refers to microbial cultures which, when ingested in the form of viable cells by humans or animals, confer an improved health condition, e.g. by suppressing harmful microorganisms in the gastrointestinal tract, by enhancing the immune system or by contributing to the digestion of nutrients. Probiotics may also be administered to plants. Probiotic cultures may comprise bacteria and/or fungi.

Lactic Acid Bacteria (LAB)

In the present context, the term "lactic acid bacteria (LAB)" refers to a group of Gram positive, catalase negative, non-motile, microaerophilic or anaerobic bacteria that ferment sugar with the production of acids including lactic acid as the predominantly produced acid, acetic acid, formic acid and propionic acid. The industrially most useful lactic acid bacteria include, but are not limited to, *Lactococcus* species (spp.), *Streptococcus* spp., *Lactobacillus* spp., *Leuconostoc* spp., *Pediococcus* spp., *Brevibacterium* spp, *Enterococcus* spp. and *Propionibacterium* spp. Additionally, lactic acid producing bacteria belonging to the group of the strict anaerobic bacteria, Bifidobacteria, i.e. *Bifidobacterium* spp. which are frequently used as food starter cultures alone or in combination with lactic acid bacteria, are generally included in the group of lactic acid bacteria. Even certain bacteria of the genus *Staphylococcus* (e.g. *S. carnosus, S. equorum, S. sciuri, S. vitulinus* and *S. xylosus*) have been referred to as LAB (Seifert & Mogensen (2002)).

Encapsulation Matrix and Matrix Components

In the present context, the term "encapsulation matrix" refers to the coating or layer enclosing the microbial culture. The coating or layer comprises one or more matrix components.

Preferably, all matrix components of the encapsulation matrix are food graded, such as complying with the Food Chemicals Codex (FCC) and/or Generally Recognized as Safe (GRAS) ingredients. Matrix components include, but are not limited to, antioxidants, cryoprotectants, carbohydrates, proteins, alone or in combination between each other.

Microencapsulated

In the present context, the term "microencapsulated" refers to an entity, which on a micrometric scale is secluded from the surrounding environment. Thus, a microencapsulated microbial culture is a microbial culture which are compartmentalized into distinct entities separated from each other and the medium into which they are dispersed.

Coacervate

In the present context, the term "coacervate" refers to an aqueous phase (or droplet) rich in the microbial culture. In the present context, coacervates are formed when a non-homogeneous (phase separated) encapsulation matrix is applied. In turn, coacervates are then formed due to liquid-liquid phase separation providing a dense phase (or droplets) and a dilute phase in thermodynamic equilibrium with each other. This process is also known as segregative phase separation.

Thus, a coacervation formulation as described herein refers to a formulation of coacervates comprising the microbial culture.

Coacervates as used herein are to be distinguished from complex coacervates, which are limited to a distinct form of coacervates formed by the electrostatic interactions of biopolymers of opposite charge. This process is also known as associative phase separation.

Viability

In the present context, the term "viability" refers to living cells in a culture. Thus, the viability of a cell culture may be determined by measuring the number of colony forming units (CFU). CFU refer to the number of individual colonies of any microbe that grow on a plate of media. This value in turn represents the number of bacteria or fungi capable of replicating as they have formed colonies on the plate.

Viable cell counts are determined in freeze-dried sampled immediately after freeze-drying and at selected time points during the stability studies. A standard pour-plating method is used. In brief, a known amount of sample is homogenized with a specific volume of diluent (1:100), using a stomacher, the solution is then resuspended by using a vortex mixer and is then subjected to decimal dilutions in peptone saline diluent (also referred to as 'maximum recovery diluent (MRD)'). MRD comprises peptone, NaCl and demineralised water. Dilutions are poured on the plates, mixed with MRS Agar (Hi-media, M641) and incubated anaerobically for three days at 37° C. After incubation, colonies are counted manually. The result is reported as average CFU/g freeze-dried sample, calculated from the duplicates.

Antioxidant

In the present context, the term "antioxidant" refers to a compound that inhibit oxidation. The antioxidant may be industrial chemicals or natural compounds. As used herein, antioxidants include, but are not limited to, trisodium citrate, vitamin C, vitamin E, glutathione, ascorbate, ascorbyl palmitate, quercetin, gallic acid, and tocotriene.

It is to be understood that antioxidants as used herein include mineral salts of vitamin C, such as sodium ascorbate. Also, the vitamin E is to be understood as including all variants of tocopherols and tocotrienols (alpha, beta, gamma, delta).

Hydrophobic Coating

In the present context, the term "hydrophobic coating" refers to a hydrophobic layer or shell that is positioned on the surface of the coacervate. Such hydrophobic layer or shell may comprise one or more hydrophobic compounds or molecules comprising a hydrophobic moiety that cause the outer surface of the coacervate to be hydrophobic.

The hydrophobic coating may comprise, but is not limited to, fats and waxes, such as carnauba wax, beeswax, coco butter fat, hydrogenated palm oil, palm stearin, shea butter fat, mango butter fat, soya oil, olive oil, coconut oil, rice bran oil, sunflower oil, candelilla wax, rice bran wax and laurel wax.

Food-Grade Ingredient

In the present context, the term "food-grade ingredient" refers to any compound that is non-toxic and safe for consumption and comply with the Food Chemicals Codex (FCC) and/or Generally Recognized as Safe (GRAS) ingredients. Food-grade ingredients include, but are not limited to, compounds that can alter attributes such as aroma, flavour, acidity, colour, viscosity and texture, as well as preservatives, nutrients, thickeners, sweeteners and emulsifiers.

Pharmaceutical Ingredient

In the present context, the term "pharmaceutical ingredient" refers to an ingredient in a pharmaceutical formulation that is not an active ingredient.

Pharmaceutical ingredients include, but are not limited to, calcium carbonate, sodium carboxymethyl cellulose, talc, polydimethylsiloxane, hydroxypropyl cellulose and hydroxypropyl methylcellulose.

Excipient

In the present context, the term "excipient" refers to a natural or synthetic substance formulated alongside the active ingredient or pharmaceutical ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing solubility, adjusting tonicity, mitigating injection site discomfort, depressing the freezing point, or enhancing stability.

Examples of excipients include, but are not limited to, microcrystalline cellulose, titanium dioxide and aluminium silicate.

Feed

In the present context, the term "feed" refers to a food given to domestic animals. Domesticated animals include, but are not limited to, pets, such as dogs, cats, rabbits, hamsters and the like, livestock, such as cattle, sheep, pigs, goats and the like, and beast of burden, such as horses, camels, donkeys and the like.

Feed may be blended from various raw materials and additives and specifically formulated according to the requirements of the recipient animal. Feed may be provided e.g. in the form of mash feed, crumbled feed or pellet feed.

The term "feed" includes also premixes, which are composed of ingredients such as vitamins, minerals, chemical preservatives, antibiotics, fermentation products and combinations thereof. Premixes are typically added as a nutritional supplement to the feed given to the domestic animals.

Water Activity

In the present context, the term "water activity" refers to the partial vapour pressure of water in a substance divided by the standard state partial vapour pressure of water. The water activity is denoted Aw. Specifically, Aw of a food is the ratio between the vapor pressure of the microencapsulated microbial culture itself, when in a completely undisturbed balance with the surrounding air media, and the vapor pressure of distilled water under identical conditions.

As a general note, water migrates from areas of high Aw to areas of low Aw. The storage stability of food products can typically be extended by formulating the product with low Aw.

Water activity as referred to herein is measured using a Rotronics water activity analyzer with HC2-AW probe. This probe is fitted with a HYGROMER® WA-1/Pt-100, 1/3 DIN Class B humidity sensor and the psychrometric calculations are done by the dew or frost point method.

Briefly, a sample is placed into a sample cup and filled up to within 3 mm of the rim while ensuring as less air in the container as possible to ensure a faster equilibration time. Next, the measurement head is placed on the sample holder ensuring a tight seal. The water activity is the measured using a predictive model of the Rotronic water activity analyser.

The water activity is calculated using the following formulae: $Aw=p/p_s$ and % $ERH=100\times Aw$, where, p=partial pressure of water vapor at the surface of the product; $p_s$=saturation vapor/partial pressure of water vapor above pure water at the product temperature; ERH=Equilibrium Relative Humidity.

Storage Stability

In the present context, the term "storage stability" refers to the ability of a microencapsulated microbial culture to maintain viability when stored at accelerated storage conditions over an extended duration of time, such as at a temperature of 37° C. and a water activity (Aw)≤0.4 for a period of 2 weeks.

Storage stability can be determined by analysing how the count of viable microbial cells develop over time. Viability of the microbial culture is measured by determining the CFU/g as described herein. Thus, a measure of the storage stability of the microencapsulated microbial culture may be determined by evaluating CFU/g of the granulates of microencapsulated microbial culture at time point 0 (just after drying) and after 2 weeks (or 4 weeks) of storage at accelerated storage conditions.

In brief, the storage stability of FD grinded powder is investigated as follows; A sample of FD granulates of microbial culture is grinded in a coffee blender for 30 seconds and passed through a #60 mesh (250μ) sieve, followed by 100-fold dilution in $CaCO_3$ to achieve a sample with a water activity (Aw) of 0.4. The sample is placed in an aluminium bag and the bag is sealed so that no air is trapped within it. The bag is stored at 37° C. for 2 weeks (or 4 weeks) and the CFU/g is determined for the sample.

Microencapsulated Microbial Cultures, Compositions Comprising the Same and Methods for their Production Microbial cultures, such as lactic acid bacteria (LAB), play key parts in many fermented products, in which they add nutritional value to the product and improve the organoleptic and textural profile of e.g. food products. The microbial cultures are typically acquired separately as powdered compositions and mixed with additional ingredients to yield a final product. Thus, the powdered composition comprising the microbial culture need as a minimum to maintain viability from the point of becoming a dried granulate to the point at which the powdered microbial cultures is included in a final product. Ideally, the microbial cultures are kept refrigerated during transport, supplementary processing and as part of the final product. However, this is not always possible as cold transport and storage is both expensive and, in many cases, not feasible in e.g. developing countries or remote regions. Moreover, the final product may be an article that is not readily stored under refrigerated conditions. This is typically the case of animal feed.

To deliver microbial cultures of high quality, e.g. high viability, under such environmental stress conditions, it is a necessary to decrease yield loss during downstream processing and eliminate the requirement of refrigerated transport and storage. However, no methods exist that both provide adequate cryo/lyo protection and enhance storage stability at elevated temperatures.

Herein are provided methods for microencapsulation of microbial cultures in an encapsulation matrix which secludes the microbial culture from the surrounding environment. The microbial cultures are entrapped at high ratios of encapsulation matrix to core material, which lead to preserved viability of the microencapsulated microbial culture over extended periods of storage at elevated temperatures.

Thus, an aspect of the present invention relates to a microencapsulated microbial culture, wherein said microbial culture is entrapped in a coacervate comprising:

i) a core material comprising a microbial culture, and ii) an encapsulation matrix comprising one or more matrix components, wherein the ratio (wt %/wt %) of encapsulation matrix to core material is at least 2.

The ratio (wt %/wt %) of encapsulation matrix material to core material in the formulation is also referred to as the encapsulation index (EI). Without being bound by theory, it is contemplated that microencapsulated microbial cultures formulated at high EI will more efficiently restrict absorption of water and thereby yield increased storage stability.

Thus, an embodiment of the present invention relates to the microencapsulated microbial culture as described herein, wherein the ratio (wt %/wt %) of encapsulation matrix to core material is the range of 2-10, such as in the range of 2-8, such as in the range of 4-8.

Another embodiment of the present invention relates to the microencapsulated microbial culture as described herein, wherein the ratio (wt %/wt %) of encapsulation matrix to core material is at least 3, preferably at least 4.

The core material may in some variants consist exclusively of microbial culture. Therefore, the microencapsulated microbial culture may also be defined in terms of the ratio (wt %/wt %) of encapsulation matrix to microbial culture. Accordingly, an embodiment of the present invention relates to the microencapsulated microbial culture as described herein, wherein the ratio (wt %/wt %) of encapsulation matrix to microbial culture is at least 2, such as at least 3, preferably at least 4.

The encapsulation matrix may preferably comprise more than a single component. Combination of encapsulation matrix components with different chemical properties allow microencapsulation to be tailored to the specific microbial culture or to a specific application. Therefore, an embodiment of the present invention relates to the microencapsulated microbial culture as described herein, wherein the encapsulation matrix comprises at least two matrix components, such as at least three matrix components, such as at least four matrix components.

The encapsulation matrix and its components are selected so that aqueous droplets (coacervates) are formed upon mixing with the microbial culture. These coacervates are rich in the microbial culture. A non-homogeneous encapsulation matrix may preferably be used to form the coacervates. By non-homogeneous matrix is meant a matrix comprising components which upon mixing will not mix homogeneously but instead separate in discrete phases. Thus, an embodiment of the present invention relates to the microencapsulated microbial culture as described herein, wherein the encapsulation matrix is a non-homogenous matrix.

The matrix components may in addition to driving the formation of the coacervation formulation serve as cryoprotectants and/or antioxidants to further enhance resistance of the microbial culture to processing and storage. Accordingly, and embodiment of the present invention relates to the microencapsulated microbial culture as described herein, wherein the one or more matrix components are selected from the group consisting of carbohydrates, proteins, antioxidants, and combinations thereof.

Cryoprotectants are used to improve the ability of microbial culture concentrates to survive against the harmful effect of freezing, frozen storage and freeze-drying. Preferably, these cryoprotectants should not be metabolized by the microbial strain to produce acids as it may cause a loss of viability due to damage to ATPase membrane-bound enzymes, β-galactosidase, and cell membrane fluidity. In general, cryoprotectants that are not producing acids are more effective in improving the survival rate of freeze-dried microbial cultures. One preferred category of cryoprotectants is carbohydrates and the associated subgroups thereof.

Therefore, an embodiment of the present invention relates to the microencapsulated microbial culture as described herein, wherein the carbohydrates are selected from the group consisting of monosaccharides, disaccharides, oligosaccharides, polysaccharides, and combinations thereof.

Another embodiment of the present invention relates to the microencapsulated microbial culture as described herein, wherein the monosaccharides are selected from the group consisting of glucose, fructose, galactose, fucose, xylose, erythrose, and combinations thereof.

Yet another embodiment of the present invention relates to the microencapsulated microbial culture as described herein, wherein the disaccharides are selected from the group consisting of trehalose, lactose, sucrose, maltose, cellobiose, and combinations thereof. A preferred embodiment of the present invention relates to the microencapsulated microbial culture as described herein, wherein the disaccharide is trehalose.

A further embodiment of the present invention relates to the microencapsulated microbial culture as described herein, wherein the oligosaccharides are selected from the group consisting of fructo-oligosaccharides (FOS), galactooligosaccharides (GOS), mannan oligosaccharides (MOS), and combinations thereof.

A still further embodiment of the present invention relates to the microencapsulated microbial culture as described herein, wherein the polysaccharides are selected from the group consisting of pectin, cellodextrin, gums, alginate, starch, glycogen, cellulose, chitin, inulin, dextran, carrageenan, chitosan, and combinations thereof. A preferred embodiment of the present invention relates to the microencapsulated microbial culture as described herein, wherein the polysaccharide is pectin.

An even further embodiment of the present invention relates to the microencapsulated microbial culture as described herein, wherein the gums are selected from the group consisting of gum arabic, agar, alginate, cassia, dammar, beta-glucan, glucomannan, mastic, chicle, psyllium, spruce, gellan, guar, locust bean, xanthan, and combinations thereof.

Thus, an embodiment of the present invention relates to the microencapsulated microbial culture as described herein, wherein the proteins are selected from the group consisting of caseinate, whey proteins, gelatine, plant proteins such as pea protein, potato protein, and rice protein, and combinations thereof. A preferred embodiment of the present invention relates to the microencapsulated microbial culture as described herein, wherein the protein is sodium caseinate.

Oxidation is the loss of electrons of an atom or ion. In the present context, oxidation refers to oxidation of molecular oxygen and means that oxygen is metabolised to unstable free radicals, which can pry away electrons from other molecules. Oxidation may therefore lead to damaging of cell membranes and other cellular components, such as proteins, lipids and DNA. To avoid damage to the microencapsulated microbial culture, one or more antioxidants may be included in the encapsulation matrix to prevent oxidation. The antioxidants may be of either natural or synthetic origin.

Therefore, an embodiment of the present invention relates to the microencapsulated microbial culture as described herein, wherein the antioxidants are selected from the group consisting of citrate, ascorbate, tocopherol, ascorbyl palmitate, quercetin, gallic acid, tocotriene, tocotrienol, glutathione, and combinations thereof.

Another embodiment of the present invention relates to the microencapsulated microbial culture as described herein, wherein the antioxidants are selected from vitamin C and/or vitamin E. It is to be understood that antioxidants as used herein include mineral salts of vitamin C, such as sodium ascorbate. Also, the vitamin E is to be understood as including all variants of tocopherols and tocotrienols (alpha, beta, gamma, delta).

Yet another embodiment of the present invention relates to the microencapsulated microbial culture as described herein, wherein the antioxidants are selected from trisodium citrate and/or sodium ascorbate. A preferred embodiment of the present invention relates to the microencapsulated microbial culture as described herein, wherein the antioxidant is trisodium citrate.

One encapsulation matrix that has been surprisingly efficient in providing microbial cultures with enhanced storage stability when kept at ambient storage conditions comprises four encapsulation matrix components (see Example 2). Thus, a preferred embodiment of the present invention relates to the microencapsulated microbial culture as described herein, wherein the encapsulation matrix comprises sodium caseinate, pectin, trehalose and trisodium citrate.

The content of encapsulation matrix components may be tailored to the specific microbial culture to be encapsulated and the expected application of the final powdered product. If the microencapsulated microbial culture is intended for an application for which extended storage is expected, it may for instance be preferable to increase the content of antioxidants. The content of antioxidants may also be adjusted depending on the conditions of storage, e.g. the degree of exposure to air. Likewise, the combination and content of cryoprotectants may be adjusted to suit the specific choice of cryo-processing. It is to be understood that the content of each encapsulation matrix component is given as the wt % with respect to the total weight of the encapsulation matrix.

Therefore, an embodiment of the present invention relates to the microencapsulated microbial culture as described herein, wherein the content of sodium caseinate in the encapsulation matrix is between 1-6 wt %, such as between 2-5 wt %, preferably between 3-4 wt %.

Another embodiment of the present invention relates to the microencapsulated microbial culture as described herein, wherein the content of pectin in the encapsulation matrix is between 0.5-3 wt %, such as between 0.75-2.5 wt %, preferably between 1-2 wt %.

A further embodiment of the present invention relates to the microencapsulated microbial culture as described herein, wherein the content of trehalose in the encapsulation matrix is between 10-40 wt %, such as between 15-35 wt %, preferably between 20-30 wt %.

An even further embodiment of the present invention relates to the microencapsulated microbial culture as described herein, wherein the content of trisodium citrate in the encapsulation matrix is between 1-10 wt %, such as between 2-8 wt %, preferably between 4-6 wt %.

Yet another embodiment of the present invention relates to the microencapsulated microbial culture as described herein, wherein the encapsulation matrix comprises between 1-6 wt % sodium caseinate, between 0.5-3 wt % pectin, between 10-40 wt % trehalose, and between 1-10 wt % trisodium citrate.

It is the high amount of encapsulation matrix and selection of encapsulation matrix components that drives the microencapsulation process via coacervation and gives enhanced storage stability at ambient storage conditions. Accordingly, the microencapsulation technique presented herein is not limited to a specific type of microbial culture but is a general microencapsulation concept. Thus, it is contemplated that any type of microbial culture may advantageously be microencapsulated as described herein.

Two types of microorganisms that are of great importance in many consumer goods are bacteria and yeast. These microorganisms are included e.g. in fermented food, feed mixes and nutritional supplements, wherein their health benefits are well-documented.

Therefore, an embodiment of the present invention relates to the microencapsulated microbial culture as described herein, wherein the microbial culture is a bacterium or a yeast.

Another embodiment of the present invention relates to the microencapsulated microbial culture as described herein, wherein the microbial culture is or comprises a genus selected from the group consisting of *Lactobacillus, Leuconostoc, Pediococcus, Lactococcus, Streptococcus, Enterococcus, Bifidobacterium, Propionibacterium, Brevibacterium, Staphylococcus, Bacillus* and *Saccharomyces.*

Of particular interest are lactic acid bacteria (LAB) that are an order of Gram-positive bacteria sharing common metabolic and physiological characteristics. LAB produce lactic acid as the major metabolic outcome of carbohydrate fermentation. Ever since it was discovered that acidification by food fermentation could preserve food by inhibiting growth of spoilage agents, LAB has been utilized purposefully in food fermentation. However, since efficient food fermentation requires high quality viable microorganisms, the development of fermented foods has been halted in areas that do not have advanced facilities to handle the fragile microorganisms. Specifically, microbial cultures, such as LAB, are not easily handled in some developing countries or remote regions due to the requirement and cost of refrigerated facilities. The microencapsulated microbial cultures described herein tolerate storage at elevated temperatures and may thus open up development of products containing microbial cultures, such as LAB, to a broader ensemble of product developers.

Thus, an embodiment of the present invention relates to the microencapsulated microbial culture as described herein, wherein the microbial culture is a lactic acid bacteria (LAB). Another embodiment of the present invention relates to the microencapsulated microbial culture as described herein, wherein the microbial culture is or comprises a lactic acid bacteria (LAB) of a genus selected from the group consisting of *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liguorilactobacillus, Ligilactobacillus, Lactiplantibacillus, Furfurilactobacillus, Paucilactobacillus, Limosilactobacillus, Fructilactobacillus, Acetilactobacillus, Apilactobacillus,*

*Levilactobacillus, Secundilactobacillus and Lentilactobacillus, Leuconostoc, Pediococcus, Lactococcus, Streptococcus, Enterococcus, Bifidobacterium, Brevibacterium*, and *Staphylococcus*.

It will be appreciated that the *Lactobacillus* genus taxonomy was updated in 2020. The new taxonomy is disclosed in Zheng et al. 2020 and will be cohered to herein if nothing else is noticed. For the purpose of the present invention, Table 1 presents a list of new and old names of some *Lactobacillus* species relevant to the present invention.

TABLE 1

New and old names of some *Lactobacillus* species relevant to the present invention

| Old Name | New Name |
|---|---|
| *Lactobacillus reuteri* | *Limosilactobacillus reuteri* |
| *Lactobacillus rhamnosus* | *Lacticaseibacillus rhamnosus* |
| *Lactobacillus salivarius* | *Ligilactobacillus salivarius* |
| *Lactobacillus casei* | *Lacticaseibacillus casei* |
| *Lactobacillus paracasei* subsp. *paracasei* | *Lacticaseibacillus paracasei* subsp. *Paracasei* |
| *Lactobacillus plantarum* subsp. *plantarum* | *Lactiplantibacillus plantarum* subsp. *plantarum* |
| *Lactobacillus fermentum* | *Limosilactobacillus fermentum* |
| *Lactobacillus animalis* | *Ligilactobacillus animalis* |
| *Lactobacillus buchneri* | *Lentilactobacillus buchneri* |
| *Lactobacillus curvatus* | *Latilactobacillus curvatus* |
| *Lactobacillus futsaii* | *Companilactobacillus futsaii* |
| *Lactobacillus sakei* subsp. *sakei* | *Latilactobacillus sakei* subsp. |
| *Lactobacillus pentosus* | *Lactiplantibacillus pentosus* |

Bacteria of the *Lactobacillus* genus, as well as the related newly updated genera, have for a long time been known to constitute a significant component of the microbiota in the human body, such as in the digestive system, urinary system and genital system. For this reason, these bacteria have been heavily utilized in in health and/or nutritional products aimed at aiding, maintaining or restoring the natural balance of microbiota in the human body. Examples of application of *Lactobacillus* include treatment or amelioration of diarrhea, vaginal infections, and skin disorders such as eczema.

Thus, an embodiment of the present invention relates to the microencapsulated microbial culture as described herein, wherein the microbial culture is or comprises a lactic acid bacteria (LAB) of a genus selected from the group consisting of *Lactobacillus, Limosilactobacillus, Lacticaseibacillus, Ligilactobacillus, Lacticaseibacillus, Lacticaseibacillus, Lactiplantibacillus, Limosilactobacillus, Ligilactobacillus, Lentilactobacillus, Latilactobacillus, Cornpanilactobacillus, Latilactobacillus* and *Lactiplantibacillus*. Another embodiment of the present invention relates to the microencapsulated microbial culture as described herein, wherein the microbial culture is or comprises a species of *Limosilactobacillus reuteri, Lacticaseibacillus rhamnosus, Ligilactobacillus salivarius, Lacticaseibacillus casei, Lacticaseibacillus paracasei* subsp. *paracasei, Lactiplantibacillus plantarum* subsp. *plantarum, Limosilactobacillus fermentum, Ligilactobacillus animalis, Lentilactobacillus buchneri, Latilactobacillus curvatus, Cornpanilactobacillus futsaii, Latilactobacillus sakei* subsp., *Lactiplantibacillus pentosus, Lactobacillus* acidophillus, *Lactobacillus helveticus, Lactobacillus* gasseri and *Lactobacillus delbrueckii.*

Yet another embodiment of the present invention relates to the microencapsulated microbial culture as described herein, wherein the microbial culture is or comprises *Ligilactobacillus animalis* deposited as DSM 33570 at Leibniz Institute DSMZ-German Collection of Microorganisms and Cell cultures Inhoffenstr. 7B 38124 Braunschweig Germany (Deutsche Sammlung von Mikroorganismen and Zellkulturen (DSMZ) 5 GmbH1 Inhoffenstr. 7B, D-38124 Braunschweig, Germany) by Chr. Hansen A/S, Horsholm, Denmark on 8 Jul. 2020.

Probiotic culture are cultures of live microorganisms, which upon ingestion by a subject provide health benefits to the subject. A probiotic microorganism may be a LAB. Products comprising probiotic cultures include dairy products, animal feed and beverages. Thus, it is to be understood that the microencapsulated microbial cultures described herein may be administered not only to humans but also animals, and even plants.

Thus, an embodiment of the present invention relates to the microencapsulated microbial culture as described herein, wherein the microbial culture is a probiotic culture.

Another embodiment of the present invention relates to the microencapsulated microbial culture as described herein, wherein the probiotic culture is of a genus selected from the group consisting of *Lactobacillus* or *Bifidobacterium.*

Yet another embodiment of the present invention relates to the microencapsulated microbial culture as described herein, wherein the probiotic culture is selected from the group consisting of *Lacticaseibacillus rhamnosus, Ligilactobacillus animalis* and *Bifidobacterium animalis* subsp. *Lactis.*

Another embodiment of the present relates to the microencapsulated microbial culture as described herein, wherein the microencapsulated microbial culture is a dry preparation.

A further embodiment of the present invention relates to the microencapsulated microbial culture as described herein, wherein the dry preparation is selected from the group consisting of a freeze-dried, spray dried, vacuum dried and air-dried preparation.

Yet another embodiment of the present invention relates to the microencapsulated microbial culture as described herein, wherein the dry preparation is freeze-dried.

Environmental conditions may be controlled during the microencapsulation to provide coacervates of high stability. Thus, an embodiment of the present invention relates to the microencapsulated microbial culture as described herein, wherein the pH of the microencapsulated microbial culture is in the range between 6-8, preferably between 6.25-7.5. Another embodiment of the present invention relates to the microencapsulated microbial culture as described herein, wherein the pH of the microencapsulated microbial culture is at least 6, such as at least 6.25, such as at least 6.5.

Storage stability may be further increased by applying a hydrophobic coating on the exterior of the microencapsulated microbial culture. Thus, an embodiment of the present invention relates to the microencapsulated microbial culture as described herein further comprising a hydrophobic coating. Another embodiment of the present invention relates to the microencapsulated microbial culture as described herein, wherein the hydrophobic coating comprises one or more fats or waxes, or mixtures thereof. A further embodiment of the present invention relates to the microencapsulated microbial culture as described herein, wherein the hydrophobic coating comprises one or more ingredients selected from carnauba wax, beeswax, coco butter fat, hydrogenated palm oil, palm stearin, shea butter fat, mango butter fat, soya oil, olive oil, coconut oil, rice bran oil, sunflower oil, candelilla wax, rice bran wax, laurel wax, and combinations thereof.

To exert its beneficial effect, it is preferred that the core material is of high quality and comprises significant amounts of viable microbial culture. These will contribute to the functions regulated by the natural population of live microbes within the consumer, such as in the intestines. Therefore, an embodiment of the present invention relates to the microencapsulated microbial culture as described herein, wherein the core material comprises in the range of 1.0E+07 to 5.0E+11 CFU/g microbial culture, preferably in the range of 1.0E+09 to 1.0E+11 CFU/g microbial culture, more preferably in the range of 1.0E+10 to 5.0E+10 CFU/g microbial culture.

The microencapsulated microbial culture may be diluted with $CaCO_3$ for certain applications, e.g. within the feed industry. Thus, an embodiment of the present invention relates to the microencapsulated microbial culture as described herein, wherein the microencapsulated microbial culture is diluted at least 10-fold with $CaCO_3$, such as diluted at least 20-fold with $CaCO_3$, such as diluted at least 50-fold with $CaCO_3$, such as diluted at least 100-fold with $CaCO_3$, such as diluted at least 1000-fold with $CaCO_3$. Another embodiment of the present invention relates to the microencapsulated microbial culture as described herein, wherein it is a freeze-dried preparation of the microencapsulated microbial culture that is diluted.

The combination of encapsulation matrix components and careful selection of process parameters has resulted in microencapsulated microbial cultures that readily withstand drying and storage at harsh conditions for extended periods of time. Accordingly, the compositions and products described herein are especially suitable for distribution to areas where cooling is not possible. The count of viable microbes after storage is the most important product quality to the downstream developer or consumer. Thus, an embodiment of the present invention relates to the microencapsulated microbial culture as described herein, wherein the microbial culture comprises a content of viable microbes in the range from 1.0E+06 to 1.0E+11 CFU/g after storage for 2 weeks at 37° C. and Aw≤0.4. Another embodiment of the present invention relates to the microencapsulated microbial culture as described herein, wherein the microbial culture comprises a content of viable microbes of at least 1.0E+05 CFU/g, such as at least 1.0E+06 CFU/g, such as at least 1.0E+07 CFU/g, such as at least 1.0E+08 CFU/g, preferably at least 1.0E+09 CFU/g, more preferably at least 1.0E+10 CFU/g after storage for 4 weeks at 37° C. and Aw≤0.15.

Yet another embodiment of the present invention relates to the microencapsulated microbial culture as described herein, wherein the loss in viability of the microbial culture as measured by CFU/g is less than 3 log units after storage for 2 weeks at 37° C. and Aw≤0.4, preferably less than 2.5 log unit after storage for 2 weeks at 37° C. and Aw≤0.4.

The microencapsulated microbial culture will typically be utilized as an additive in an end product comprising also other ingredients. It is therefore contemplated that the microencapsulated microbial culture for many applications will be part of a more complex composition. Thus, an aspect of the present invention relates to a composition comprising the microencapsulated microbial culture as described herein.

As the microencapsulated microbial culture is admixed with other ingredients the coacervates formed during the mixing of encapsulation matrix and core material stay intact to safeguard the microbial culture from any environment potentially harmful to the microorganisms. Therefore, an embodiment of the present invention relates to the composition as described herein, wherein the composition comprises coacervates comprising the microbial culture and the encapsulation matrix.

The microencapsulated microbial culture may be utilized for many different types of applications spanning from e.g. health products, nutritional supplement and pharmaceutics to animal feed. Thus, a composition encompassing the microencapsulated microbial culture may comprise a wide range of additives. Therefore, an embodiment of the present invention relates to the composition as described herein, wherein the composition further comprises one or more additives selected from the group consisting of food-grade ingredients, feed-grade ingredients, pharmaceutical ingredients and excipients.

Food-grade ingredients are compounds that are non-toxic and safe for consumption and comply with the Food Chemicals Codex (FCC). Food-grade ingredients include, but are not limited to, compounds that can alter attributes such as aroma, flavour, acidity, colour, viscosity and texture, as well as preservatives, nutrients, thickeners, sweeteners and emulsifiers.

An embodiment of the present invention relates to the composition, product or dairy product as described herein, wherein the one or more food-grade ingredients are selected from the group consisting of compounds that can alter attributes such as aroma, flavour, acidity, colour, viscosity and texture, as well as preservatives, nutrients, thickeners, sweeteners, emulsifiers, and combinations thereof.

Another embodiment of the present invention relates to the composition as described herein, wherein the food-grade ingredients are selected from the group consisting of lactose, maltodextrin, whey protein, casein, corn starch, dietary fibres, gums and gelatine.

A further embodiment of the present invention relates to the composition as described herein, wherein the pharmaceutical ingredients are selected from the group consisting of calcium carbonate, sodium carboxymethyl cellulose, talc, polydimethylsiloxane, hydroxypropyl cellulose and hydroxypropyl methylcellulose.

Yet another embodiment of the present invention relates to the composition as described herein, wherein the excipients are selected from the group consisting of microcrystalline cellulose, titanium dioxide and aluminium silicate.

Many additives are provided in dry powder form to extent the shelf life and ease the handling of the additive. The microencapsulated microbial culture is no exception and may preferably be provided in dry form. Therefore, an embodiment of the present invention relates to the composition as described herein, wherein the composition is a dry preparation.

The dry powder preparation comprising microbial culture may be obtained using any suitable method which does not significantly diminish viability of the microbial culture. Accordingly, an embodiment of the present invention relates to the composition as described herein, wherein the composition is a freeze-dried composition.

A still further embodiment of the present invention relates to the microencapsulated microbial culture or the composition as described herein, wherein the microencapsulated microbial culture or composition is in the form of a powder and/or a granulate.

Keeping the water activity of the dried preparation low will contribute to the dry preparation not being spoiled over time. By controlling the water activity (Aw), it is possible to predict and regulate the effect of moisture migration on the product. In general, a water activity of less than 0.6 should avoid any unwanted microorganisms to proliferate. Therefore, an embodiment of the present invention relates to the microencapsulated microbial culture or the composition as described herein, wherein the water activity (Aw) of the microencapsulated microbial culture is in the range from 0.01-0.8, preferably in the range from 0.05-0.6, most preferably in the range from 0.1-0.4.

Microbial cultures may find diverse application across many different consumer sectors. Therefore, an aspect of the present invention relates to a product comprising the microencapsulated microbial culture or the composition as described herein, wherein the product is selected from the group consisting of a feed, a plant health product, a food, a beverage and a pharmaceutical product.

Especially the utilization of the microencapsulated microbial culture in animal feed is a preferred application. Thus, an embodiment of the present invention relates to a product comprising the microencapsulated microbial culture or the composition as described herein, wherein the product is a feed product selected from the group consisting of a feed premix, a feed blend, a pet food and a domestic animal feed.

It is to be understood that the term "food" includes also "extruded food products" and "bars", and that "food" or "feed" may be in the form of a pre-mix that is intended to be further mixed with additional ingredients to obtain a final product. Thus, an embodiment of the present invention relates to the product or the composition as described herein, wherein the product or composition is a pre-mix. Another embodiment of the present invention relates to the product or the composition as described herein, wherein the product or composition is an extruded food product or a bar. A bar is a texturized product made by extrusion where different food components are held together with edible adhesives, such as, but not limited to, sugars.

Any of such products may comprise further excipients suitable for any specific type of products. Such excipients include, but are not limited to, lactose, rice hull and microcrystalline cellulose (MCC).

Another preferred area of application is within products comprising LAB. Therefore, an embodiment of the present invention relates to a product comprising the microencapsulated microbial culture or the composition as described herein, wherein the product is a fermented product.

Probiotic-containing products are also a prioritized field of application. Thus, an aspect of the present invention relates to a dairy product comprising the microencapsulated microbial culture or the composition as described herein. Another embodiment of the present invention relates to the dairy product as described herein, wherein the dairy product selected from the group consisting of yoghurt, cheese, butter, inoculated sweet milk and liquid fermented milk products.

A milk-based product such as yogurt is a well characterized carrier suitable to protect and deliver microbial cultures, such as probiotics, in the gut. One of the reasons is that yogurt is rich in nutrients, proteins, fatty acids, carbohydrates, vitamins, minerals, and calcium, which improves the capability of the probiotic strains to bind the epithelial cell. Another reason is that the consumer considers yogurt a nutritional, healthy, and natural carrier of living bacteria, so preferably consumes it daily.

Thus, an embodiment of the present invention relates to the dairy product as described herein, wherein the dairy product is a yoghurt.

Decreasing yield loss of microbial cultures during freezing/FD downstream processing is of great importance, both in terms of quality but also in terms of process efficiency. Similarly, the ability to retain maximum viability of the microbial cultures during ambient storage conditions has commercial and technical advantages. Thus, the methods described herein has been developed with the aim of achieving both objectives. The method described herein relies on entrapment of the microbial culture within dense phase droplets (coacervates) formed by mixing high amounts of a first and second matrix. In contrast to other conventional techniques in which the microbial culture is just blended with different matrices, the method described herein provides enhanced protection of the microbial culture both during drying and ambient storage.

Thus, an aspect of the present invention relates to a method for preparing a microencapsulated microbial culture or a composition as described herein, said method comprising the steps of:

i) mixing a microbial culture with a first matrix comprising one or more first matrix components to form a first mixture, and
ii) mixing the first mixture with a second matrix comprising one or more second matrix components to form a microencapsulated microbial culture, wherein said one or more first matrix components and said one or more second matrix components are not the same.

The microbial culture may in variants of the method be mixed simultaneously with the first and second matrix, thereby forming a microencapsulated culture. Thus, an embodiment of the present invention relates to the method as described herein, wherein steps i) and ii) are performed simultaneously.

Another embodiment of the present invention relates to a method for preparing a microencapsulated microbial culture or a composition as described herein, said method comprising a step of mixing the microbial culture simultaneously with:

i) a first matrix comprising one or more first matrix components, and
ii) a second matrix comprising one or more second matrix components, to form a microencapsulated microbial culture, wherein said one or more first matrix components and said one or more second matrix components are not the same.

The first and second matrix components are selected so as to form coacervates in which the microbial culture is encapsulated upon mixing. Accordingly, together the first and second matrix components form a phase-separated encapsulation matrix. This may be achieved by using first and second matrix components having different physico-chemical properties (Example 1).

Therefore, an embodiment of the present invention relates to the method as described herein, wherein said one or more first matrix components are selected from the group consisting of carbohydrates, proteins, antioxidants, and combinations thereof.

Another embodiment of the present invention relates to the method as described herein, wherein said one or more first matrix components comprises one or more carbohydrates selected from the group consisting of monosaccharides, disaccharides, oligosaccharides, polysaccharides, and combinations thereof.

It has been found that especially disaccharides, such as trehalose, are suitable to include as first matrix components. Thus, an embodiment of the present invention relates to the method as described herein, wherein said one or more first matrix components comprises one or more disaccharides selected from the group consisting of trehalose, lactose, sucrose, maltose, cellobiose, and combinations thereof, preferably trehalose.

Likewise, it has been found that the first matrix may advantageously comprise one or more antioxidants and certain proteins. Thus, an embodiment of the present invention relates to the method as described herein, wherein said one or more first matrix components comprises one or more proteins selected from the group consisting of caseinate, whey proteins, gelatine, plant proteins such as pea protein, potato protein, and rice protein, and combinations thereof, preferably sodium caseinate.

Another embodiment of the present invention relates to the method as described herein, wherein said one or more first matrix components comprises one or more antioxidants selected from the group consisting of citrate, ascorbate, tocopherol, ascorbyl palmitate, quercetin, gallic acid, tocotriene, tocotrienol, glutathione, and combinations thereof, preferably trisodium citrate.

The second matrix may comprise one or more second matrix components. An embodiment of the present invention relates to the method as described herein, wherein said one or more second matrix components comprises one or more carbohydrates selected from the group consisting of monosaccharides, disaccharides, oligosaccharides, polysaccharides, and combinations thereof.

The inventors have found that polysaccharides, such as pectin, are suitable second matrix components. Thus, an embodiment of the present invention relates to the method as described herein, wherein said one or more second matrix components comprises one or more polysaccharides selected from the group consisting of pectin, gums, maltodextrin, cellodextrin, alginate, starch, glycogen, cellulose, chitin, inulin, dextran, carrageenan, chitosan, and combinations thereof, preferably pectin.

In some variants of the microencapsulated microbial culture, gums are a preferred second matrix component. Gums are polysaccharides capable of causing a large increase in a solution's viscosity, even when present at small concentrations. Gums may be of botanical or marine origin and can be found in both charged and non-charged variants. An embodiment of the present invention relates to the method as described herein, wherein said one or more second matrix components comprises one or more gums selected from the group consisting of gum arabic, agar, alginate, cassia, dammar, beta-glucan, glucomannan, mastic, chicle, psyllium, spruce, gellan, guar, locust bean, xanthan, and combinations thereof.

For some combinations of first and second matrices it is sufficient to use only a single component in the second matrix to obtain coacervates with a protective effect. Thus, an embodiment of the present invention relates to the method as described herein, wherein said second matrix comprises only a single second matrix component.

Many combinations of first and second matrix components can be contemplated, and the combinations demonstrated herein are not be construed as limiting to the invention. However, some selections of matrix components are preferred. Therefore, an embodiment of the present invention relates to the method as described herein, wherein said first matrix comprises sodium caseinate, trehalose and trisodium citrate.

Another embodiment of the present invention relates to the method as described herein, wherein said second matrix comprises pectin.

A preferred embodiment of the present invention relates to the method as described herein, wherein the first matrix comprises sodium caseinate, trehalose and trisodium citrate and the second matrix comprises pectin.

The first and second matrix should be provided as sterilized matrices to ensure a high-quality product and avoid contaminations. Therefore, an embodiment of the present invention relates to the method as described herein, wherein said first and second matrices are heat sterilized and subsequently cooled to ambient temperature prior to step (i).

The microbial culture of step i) may be provided as a liquid cell culture concentrate. To obtain a final dry microbial culture product with as high viability over time as possible, it is necessary to carefully select and adjust the content of the starting materials. Therefore, an embodiment of the present invention relates to the method as described herein, wherein the microbial culture of step i) is a concentrated microbial culture comprising a dry matter content in the range from 5-80 wt %, preferably 15-25 wt %. Another embodiment of the present invention relates to the method as described herein, wherein the microbial culture of step i) is a concentrated microbial culture comprising a dry matter content of at least 5 wt %, such as at least 10 wt %, such as at least 15 wt %, such as at least 20 wt %.

A further embodiment of the present invention relates to the method as described herein, wherein the microbial culture of step i) is a concentrated microbial culture comprising a content of viable microbes in the range from 1.0E+09 to 1.0E12 CFU/g, preferably approximately 1.0E11 CFU/g. A still further embodiment of the present invention relates to the method as described herein, wherein the microbial culture of step i) is a concentrated microbial culture comprising a content of viable microbes of at least 1.0E09 CFU/g, such as at least 1.0E10 CFU/g, preferably at least 1.0E11 CFU/g.

The starting materials are utilized in a coacervation process to yield the microencapsulated microbial cultures. Each process step is adjusted to obtain a coacervate formulation suitable for the intended final application, with some overall parameters, such as the temperature and duration of mixing, being defined. Thus, an embodiment of the present invention relates to the method as described herein, wherein the microbial culture of step i) is mixed with the first matrix for a time period in the range of 15 min to 2 hours at a temperature in the range of 4° C. to 20° C.

Another embodiment of the present invention relates to the method as described herein, wherein the microbial culture of step i) is mixed with the first matrix for a time period in the range of 15 min to 2 hours, such as in the range of 30 min to 2 hours, such as in the range of 1 to 2 hours.

Yet another embodiment of the present invention relates to the method as described herein, wherein the microbial culture of step i) is mixed with the first matrix at a temperature in the range of 4° C. to 20° C., such as in the range of 4° C. to 15° C., such as in the range of 4° C. to 10° C.

A further embodiment of the present invention relates to the method as described herein, wherein mixing of the first mixture with the second matrix in step ii) is carried out for a time period in the range of 15 min to 2 hours at a temperature in the range of 4° C. to 20° C.

A still further embodiment of the present invention relates to the method as described herein, wherein mixing of the first mixture with the second matrix in step ii) is carried out for a time period in the range of 15 min to 2 hours, such as in the range of 30 min to 2 hours, such as in the range of 1 to 2 hours.

An even further embodiment of the present invention relates to the method as described herein, wherein mixing of the pre-complex solution with the second matrix in step ii) is carried out at a temperature in the range of 4° C. to 20° C., such as in the range of 4° C. to 15° C., such as in the range of 4° C. to 10° C.

As an additive for inclusion in a variety of different end products, microbial cultures, such as LAB, are often supplied as dried powders. The dry form makes the microbial cultures easy to transport, store and handle prior to final processing. Therefore, an embodiment of the present invention relates to the method as described herein further comprising a step iii) subsequent to step ii), wherein step iii) comprises freezing said microencapsulated microbial culture to obtain a frozen microencapsulated microbial culture.

Another embodiment of the present invention relates to the method as described herein further comprising a step iv) subsequent to step iii), wherein step iv) comprises sublimating water from said frozen microencapsulated microbial culture to obtain a dried microencapsulated microbial culture.

A further embodiment of the present invention relates to the method as described herein, wherein step iv) is carried out by a technique selected from the group consisting of spray drying, vacuum drying, air drying, freeze drying, tray drying and vacuum tray drying.

A still further embodiment of the present invention relates to the method as described herein, wherein the technique used in step iv) is freeze drying and wherein said freeze drying is performed at a pressure in the range of 0.005 to 1 mbar and at a temperature in the range of −45° C. to 75° C. until complete water removal.

An even further embodiment of the present invention relates to the method as described herein, wherein said freeze drying is performed at a pressure in the range of 0.1 to 0.4 mbar. Yet another embodiment of the present invention relates to the method as described herein, wherein said freeze drying is performed at a pressure of at least 0.1 mbar, such as at least 0.2 mbar, such as at least 0.3 mbar, such as at least 0.4 mbar.

Another embodiment of the present invention relates to the method as described herein, wherein said freeze drying is performed at a temperature in the range of 15° C. to 35° C. An additional embodiment of the present invention relates to the method as described herein, wherein said freeze drying is performed at a temperature of at least 15° C., such as at least 20° C., such as at least 25° C., such as at least 30° C.

Depending on the application of the microencapsulated microbial culture, it may be advantageous to receive the microencapsulated microbial culture in frozen or dried form. Therefore, an embodiment of the present invention relates to the method as described herein, wherein said method further comprises:

(v) packing said frozen microencapsulated microbial culture obtained in step (iii) or the dried microencapsulated microbial culture obtained in step (iv).

The microencapsulated microbial culture is the result of the coacervation process as described herein. Consequently, an aspect of the present invention relates to a microencapsulated microbial culture or a composition obtainable by a method as described herein.

Preferably, the microencapsulated microbial culture is utilized as additive in the preparation of an end-product. Thus, an aspect of the present invention relates to the use of a microencapsulated microbial culture or a composition as described herein in a product selected from the group consisting of a feed, a plant health product, a food, a beverage and a pharmaceutical product.

The microencapsulated microbial culture is especially suited for use in dairy products in which probiotics is commonly delivered as a health supplement to the consumer.

Therefore, an embodiment of the present invention relates to the use of a microencapsulated microbial culture or a composition as described herein, wherein the product is a dairy product.

Another embodiment of the present invention relates to the use of a microencapsulated microbial culture or a composition as described herein, wherein said dairy product is selected from the group consisting of yoghurt, cheese, butter, inoculated sweet milk and liquid fermented milk products.

The listing or discussion of an apparently prior published document in this specification should not necessarily be taken as an acknowledgement that the document is part of the state of the art or is common general knowledge.

Preferences, options and embodiments for a given aspect, feature or parameter of the invention should, unless the context indicates otherwise, be regarded as having been disclosed in combination with any and all preferences, options and embodiments for all other aspects, features and parameters of the invention. This is especially true for the description of the microencapsulated microbial culture and all its features, which may readily be part of the final composition obtained by the method as described herein. Embodiments and features of the present invention are also outlined in the following items.

Items

X1. A microencapsulated microbial culture, wherein said microbial culture is entrapped in a coacervate comprising:

i) a core material comprising a microbial culture, and ii) an encapsulation matrix comprising one or more matrix components, wherein the ratio (wt %/wt %) of encapsulation matrix to core material is at least 2.

X2. The microencapsulated microbial culture according to item X1, wherein the ratio (wt %/wt %) of encapsulation matrix to core material is the range of 2-10, such as in the range of 2-8, such as in the range of 4-8.

X3. The microencapsulated microbial culture according to any one of items X1 or X2, wherein the ratio (wt %/wt %) of encapsulation matrix to core material is at least 3, preferably at least 4.

X4. The microencapsulated microbial culture according to any one of the preceding items, wherein the encapsulation matrix comprises at least two matrix components, such as at least three matrix components, such as at least four matrix components.

X5. The microencapsulated microbial culture according to any one of the preceding items, wherein the encapsulation matrix is a non-homogenous matrix.

X6. The microencapsulated microbial culture according to any one of the preceding items, wherein the one or more matrix components are selected from the group consisting of carbohydrates, proteins, antioxidants, and combinations thereof.

X7. The microencapsulated microbial culture according to item X6, wherein the carbohydrates are selected from the group consisting of monosaccharides, disaccharides, oligosaccharides, polysaccharides, and combinations thereof.

X8. The microencapsulated microbial culture according to item X7, wherein the monosaccharides are selected from the group consisting of glucose, fructose, galactose, fucose, xylose, erythrose, and combinations thereof.

X9. The microencapsulated microbial culture according to any one of items X7 or X8, wherein the disaccharides are selected from the group consisting of trehalose, lactose, sucrose, maltose, cellobiose, and combinations thereof.

X10. The microencapsulated microbial culture according to any one of items X7-X9, wherein the disaccharide is trehalose.

X11. The microencapsulated microbial culture according to any one of items X7-X10, wherein the oligosaccharides are selected from the group consisting of fructo-oligosaccharides (FOS), galactooligosaccharides (GOS), mannan oligosaccharides (MOS), and combinations thereof.

X12. The microencapsulated microbial culture according to any one of items X7-X11, wherein the polysaccharides are selected from the group consisting of pectin, cellodextrin, gums, alginate, starch, glycogen, cellulose, chitin, inulin, dextran, carrageenan, chitosan, and combinations thereof.

X13. The microencapsulated microbial culture according to any one of items X7-X12, wherein the polysaccharide is pectin.

X14. The microencapsulated microbial culture according to any one of items X12 or X13, wherein the gums are selected from the group consisting of gum arabic, agar, alginate, cassia, dammar, beta-glucan, glucomannan, mastic, chicle, psyllium, spruce, gellan, guar, locust bean, xanthan, and combinations thereof.

X15. The microencapsulated microbial culture according to any one of items X6-X14, wherein the proteins are selected from the group consisting of caseinate, whey proteins, gelatine, plant proteins such as pea protein, potato protein, and rice protein, and combinations thereof.

X16. The microencapsulated microbial culture according to any one of items X6-X15, wherein the protein is sodium caseinate.

X17. The microencapsulated microbial culture according to any one of items X6-X16, wherein the antioxidants are selected from the group consisting of citrate, ascorbate, tocopherol, ascorbyl palmitate, quercetin, gallic acid, tocotriene, tocotrienol, glutathione, and combinations thereof.

X18. The microencapsulated microbial culture according to any one of items X6-X17, wherein the antioxidant is trisodium citrate.

X19. The microencapsulated microbial culture according to any one of the preceding items, wherein the encapsulation matrix comprises sodium caseinate, pectin, trehalose and trisodium citrate.

X20. The microencapsulated microbial culture according to any one of items X16-X19, wherein the content of sodium caseinate in the encapsulation matrix is between 1-6 wt %, such as between 2-5 wt %, preferably between 3-4 wt %.

X21. The microencapsulated microbial culture according to any one of items X12-X20, wherein the content of pectin in the encapsulation matrix is between 0.5-3 wt %, such as between 0.75-2.5 wt %, preferably between 1-2 wt %.

X22. The microencapsulated microbial culture according to any one of items X9-X21, wherein the content of trehalose in the encapsulation matrix is between 10-40 wt %, such as between 15-35 wt %, preferably between 20-30 wt %.

X23. The microencapsulated microbial culture according to any one of items X18-X22, wherein the content of trisodium citrate in the encapsulation matrix is between 1-10 wt %, such as between 2-8 wt %, preferably between 4-6 wt %.

X24. The microencapsulated microbial culture according to any one of the preceding items, wherein the encapsulation matrix comprises between 1-6 wt % sodium caseinate, between 0.5-3 wt % pectin, between 10-40 wt % trehalose, and between 1-10 wt % trisodium citrate.

X25. The microencapsulated microbial culture according to any one of the preceding items, wherein the microbial culture is a bacterium or a yeast.

X26. The microencapsulated microbial culture according to any one of the preceding items, wherein the microbial culture is or comprises a lactic acid bacteria (LAB) of a genus selected from the group consisting of *Lactobacillus, Holzapfelia, Amylolactobacillus, Bombilactobacillus, Companilactobacillus, Lapidilactobacillus, Agrilactobacillus, Schleiferilactobacillus, Loigolactobacilus, Lacticaseibacillus, Latilactobacillus, Dellaglioa, Liguorilactobacillus, Ligilactobacillus, Lactiplantibacillus, Fulfurilactobacillus, Paucilactobacillus, Limosilactobacillus, Fructilactobacillus, Acetilactobacillus, Apilactobacillus, Levilactobacillus, Secundilactobacillus and Lentilactobacillus, Leuconostoc, Pediococcus, Lactococcus, Streptococcus, Enterococcus, Bifidobacterium, Brevibacterium*, and *Staphylococcus.*

X27. The microencapsulated microbial culture according to any one of the preceding items, wherein the microbial culture is or comprises a lactic acid bacterium (LAB) of a genus selected from the group consisting of *Lactobacillus, Limosilactobacillus, Lacticaseibacillus, Ligilactobacillus, Lacticaseibacillus, Lacticaseibacillus, Lactiplantibacillus, Limosilactobacillus, Ligilactobacillus, Lentilactobacillus, Latilactobacillus, Companilactobacillus, Latilactobacillus* and *Lactiplantibacillus.*

X28. The microencapsulated microbial culture according to any one of the preceding items, wherein the microbial culture is or comprises a species of *Limosilactobacillus reuteri, Lacticaseibacillus rhamnosus, Ligilactobacillus salivarius, Lacticaseibacillus casei, Lacticaseibacillus paracasei* subsp. *paracasei, Lactiplantibacillus plantarum* subsp. *plantarum, Limosilactobacillus fermentum, Ligilactobacillus animalis, Lentilactobacillus buchneri, Latilactobacillus curvatus, Cornpanilactobacillus futsaii, Latilactobacillus sakei* subsp., *Lactiplantibacillus pentosus, Lactobacillus acidophillus, Lactobacillus helveticus, Lactobacillus gasseri* and *Lactobacillus delbrueckii.*

X29. The microencapsulated microbial culture according to any one of the preceding items, wherein the microbial culture is or comprises *Ligilactobacillus animalis* deposited as DSM 33570 at Leibniz Institute DSMZ-German Collection of Microorganisms and Cell cultures Inhoffenstr. 7B 38124 Braunschweig Germany (Deutsche Sammlung von Mikroorganismen and Zellkulturen (DSMZ) 5 GmbH1 Inhoffenstr. 7B, D-38124 Braunschweig, Germany) by Chr. Hansen A/S, Horsholm, Denmark on 8 Jul. 2020.

X30. The microencapsulated microbial culture according to any one of the preceding items, wherein the microbial culture is a probiotic culture.

X31. The microencapsulated microbial culture according to any one of the preceding items, wherein the microencapsulated microbial culture is a dry preparation.

X32. The microencapsulated microbial culture according to items X31, wherein the dry preparation is selected from the group consisting of a freeze-dried, spray dried, vacuum dried and air-dried preparation.

X33. The microencapsulated microbial culture according to any one of items X31 or X32, wherein the dry preparation is freeze-dried.

X34. The microencapsulated microbial culture according to any one of the preceding items, wherein the pH of the microencapsulated microbial culture is in the range between 6-8, preferably between 6.25-7.5.

X35. The microencapsulated microbial culture according to any one of the preceding items, wherein the pH of the microencapsulated microbial culture is at least 6, such as at least 6.25, such as at least 6.5.

X36. The microencapsulated microbial culture according to any one of the preceding items further comprising a hydrophobic coating.

X37. The microencapsulated microbial culture according to item X36, wherein the hydrophobic coating comprises one or more fats or waxes, or mixtures thereof.

X38. The microencapsulated microbial culture according to any one of items X36 or X37, wherein the hydrophobic coating comprises one or more ingredients selected from carnauba wax, beeswax, coco butter fat, hydrogenated palm oil, palm stearin, shea butter fat, mango butter fat, soya oil, olive oil, coconut oil, rice bran oil, sunflower oil, candelilla wax, rice bran wax, laurel wax, and combinations thereof.

X39. The microencapsulated microbial culture according to any one of the preceding items, wherein the core material comprises in the range of 1.0E+07 to 5.0E+11 CFU/g microbial culture, preferably in the range of 1.0E+09 to 1.0E+11 CFU/g microbial culture, more preferably in the range of 1.0E+10 to 5.0E+10 CFU/g microbial culture.

X40. The microencapsulated microbial culture according to any one of the preceding items, wherein the microbial culture comprises a content of viable microbes in the range from 1.0E+06 to 1.0E+11 CFU/g after storage for 2 weeks at 37° C. and Aw 0.4.

X41. The microencapsulated microbial culture according to any one of the preceding items, wherein the loss in viability of the microbial culture as measured by CFU/g is less than 3 log units after storage for 2 weeks at 37° C. and Aw≤0.4, preferably less than 2.5 log unit after storage for 2 weeks at 37° C. and Aw≤0.4.

X42. A composition comprising the microencapsulated microbial culture according to any one of the preceding items.

X43. The composition according to item X42, wherein the composition further comprises one or more additives selected from the group consisting of food-grade ingredients, feed-grade ingredients, pharmaceutical ingredients and excipients.

X44. The composition according to item X43, wherein the food-grade ingredients are selected from the group consisting of lactose, maltodextrin, whey protein, casein, corn starch, dietary fibres, gums and gelatine.

X45. The composition according to any one of items X43 or X44, wherein the pharmaceutical ingredients are selected from the group consisting of calcium carbonate, sodium carboxymethyl cellulose, talc, polydimethylsiloxane, hydroxypropyl cellulose and hydroxypropyl methylcellulose.

X46. The composition according to any one of items X43-X45, wherein the excipients are selected from the group consisting of microcrystalline cellulose, titanium dioxide and aluminium silicate.

X47. The composition according to any one of items X42-X46, wherein the composition is a freeze-dried composition.

X48. The microencapsulated microbial culture according to any one of items X1-X41 or the composition according to any one of items X42-X47, wherein the microencapsulated microbial culture or composition is in the form of a powder and/or a granulate.

X49. The microencapsulated microbial culture according to any one of items X1-X41 or the composition according to any one of items X42-X47, wherein the water activity (Aw) of the microencapsulated microbial culture is in the range from 0.01-0.8, preferably in the range from 0.05-0.6, most preferably in the range from 0.1-0.4.

X50. A product comprising the microencapsulated microbial culture according to any one of items X1-X41 or X48-X49 or the composition according to any one of items X42-X49, wherein the product is selected from the group consisting of a feed, a plant health product, a food, a beverage and a pharmaceutical product.

X51. A dairy product comprising a microencapsulated microbial culture according to any one of items X1-X41 or X48-X49 or a composition according to any one of items

X42-X49.

X52. The dairy product according to item X51, wherein said dairy product is selected from the group consisting of yoghurt, cheese, butter, inoculated sweet milk and liquid fermented milk products.

Y1. A method for preparing a microencapsulated microbial culture according to any one of items X1-X41 or X48-X49 or a composition according to any one of items X42-X49, said method comprising the steps of:

i) mixing a microbial culture with a first matrix comprising one or more first matrix components to form a first mixture, and ii) mixing the first mixture with a second matrix comprising one or more second matrix components to form a microencapsulated microbial culture, wherein said one or more first matrix components and said one or more second matrix components are not the same.

Y2. The method according to item Y1, wherein said one or more first matrix components are selected from the group consisting of carbohydrates, proteins, antioxidants, and combinations thereof.

Y3. The method according to any one of items Y1 or Y2, wherein said one or more first matrix components comprises one or more carbohydrates selected from the group consisting of monosaccharides, disaccharides, oligosaccharides, polysaccharides, and combinations thereof.

Y4. The method according to item any one of items Y1-Y3, wherein said one or more first matrix components comprises one or more disaccharides selected from the group consisting of trehalose, lactose, sucrose, maltose, cellobiose, and combinations thereof, preferably trehalose.

Y5. The method according to item any one of items Y1-Y4, wherein said one or more first matrix components comprises one or more proteins selected from the group consisting of caseinate, whey proteins, gelatine, plant proteins such as pea protein, potato protein, and rice protein, and combinations thereof, preferably sodium caseinate.

Y6. The method according to item any one of items Y1-Y5, wherein said one or more first matrix components comprises one or more antioxidants selected from the group consisting of citrate, ascorbate, tocopherol, ascorbyl palmitate, quercetin, gallic acid, tocotriene, tocotrienol, glutathione, and combinations thereof, preferably trisodium citrate.

Y7. The method according to any one of items Y1-Y6, wherein said one or more second matrix components comprises one or more carbohydrates selected from the group consisting of monosaccharides, disaccharides, oligosaccharides, polysaccharides, and combinations thereof.

Y8. The method according to any one of items Y1-Y7, wherein said one or more second matrix components comprises one or more polysaccharides selected from the group consisting of pectin, gums, maltodextrin, cellodextrin, alginate, starch, glycogen, cellulose, chitin, inulin, dextran, carrageenan, chitosan, and combinations thereof, preferably pectin.

Y9. The method according to any one of items Y1-Y8, wherein said one or more second matrix components comprises one or more gums selected from the group consisting of gum arabic, agar, alginate, cassia, dammar, beta-glucan, glucomannan, mastic, chicle, psyllium, spruce, gellan, guar, locust bean, xanthan, and combinations thereof.

Y10. The method according to any one of items Y1-Y9, wherein said second matrix comprises only a single second matrix component.

Y11. The method according to any one of items Y1-Y10, wherein said first matrix comprises sodium caseinate, trehalose and trisodium citrate.

Y12. The method according to any one of items Y1-Y11, wherein said second matrix comprises pectin.

Y13. The method according to any one of items Y1-Y12, wherein the first matrix comprises sodium caseinate, trehalose and trisodium citrate and the second matrix comprises pectin.

Y14. The method according to any one of items Y1-Y13, wherein said first and second matrices are heat sterilized and subsequently cooled to ambient temperature prior to step (i).

Y15. The method according to any one of items Y1-Y14, wherein the microbial culture of step i) is a concentrated microbial culture comprising a dry matter content in the range from 5-80 wt %, preferably 15-25 wt %.

Y16. The method according to any one of items Y1-Y15, wherein the microbial culture of step i) is a concentrated microbial culture comprising a content of viable microbes in the range from 1.0E+09 to 1.0E12 CFU/g, preferably approximately 1.0E11 CFU/g.

Y17. The method according to any one of items Y1-Y16, wherein the microbial culture of step i) is mixed with the first matrix for a time period in the range of 15 min to 2 hours at a temperature in the range of 4° C. to 20° C.

Y18. The method according to any one of items Y1-Y17, wherein the microbial culture of step i) is mixed with the first matrix for a time period in the range of 15 min to 2 hours, such as in the range of 30 min to 2 hours, such as in the range of 1 to 2 hours.

Y19. The method according to any one of items Y1-Y18, wherein the microbial culture of step i) is mixed with the first matrix at a temperature in the range of 4° C. to 20° C., such as in the range of 4° C. to 15° C., such as in the range of 4° C. to 10° C.

Y20. The method according to any one of items Y1-Y19, wherein mixing of the first mixture with the second matrix in step ii) is carried out for a time period in the range of 15 min to 2 hours at a temperature in the range of 4° C. to 20° C.

Y21. The method according to any one of items Y1-Y20, wherein mixing of the first mixture with the second matrix in step ii) is carried out for a time period in the range of 15 min to 2 hours, such as in the range of 30 min to 2 hours, such as in the range of 1 to 2 hours.

Y22. The method according to any one of items Y1-Y21, wherein mixing of the pre-complex solution with the second matrix in step ii) is carried out at a temperature in the range of 4° C. to 20° C., such as in the range of 4° C. to 15° C., such as in the range of 4° C. to 10° C.

Y23. The method according to any one of items Y1-Y22 further comprising a step iii) subsequent to step ii), wherein step iii) comprises freezing said microencapsulated microbial culture to obtain a frozen microencapsulated microbial culture.

Y24. The method according to item Y23 further comprising a step iv) subsequent to step iii), wherein step iv) comprises sublimating water from said frozen microencapsulated microbial culture to obtain a dried microencapsulated microbial culture.

Y25. The method according to item Y24, wherein step iv) is carried out by a technique selected from the group consisting of spray drying, vacuum drying, air drying, freeze drying, tray drying and vacuum tray drying.

Y26. The method according to any one of items Y24 or Y25, wherein the technique used in step iv) is freeze drying and wherein said freeze drying is performed at a pressure in the range of 0.005 to 1 mbar and at a temperature in the range of −45° C. to 75° C. until complete water removal.

Y27. The method according to item Y26, wherein said freeze drying is performed at a pressure in the range of 0.1 to 0.4 mbar.

Y28. The method according to any one of items Y26 or Y27, wherein said freeze drying is performed at a temperature in the range of 15° C. to 35° C.

Y29. The method according to any one of items Y24-Y28, wherein said method further comprises:

(v) packing said frozen microencapsulated microbial culture obtained in step (iii) or the dried microencapsulated microbial culture obtained in step (iv).

Z1. A microencapsulated microbial culture or a composition obtainable by a method according to any one of items Y1-Y29.

Q1. Use of a microencapsulated microbial culture or a composition according to any one of items X1-X49 or Z1 in a product selected from the group consisting of a feed, a plant health product, a food, a beverage and a pharmaceutical product.

Q2. Use of a microencapsulated microbial culture or a composition according to item Q1, wherein the product is a dairy product.

Q3. Use of a microencapsulated microbial culture or a composition according to claim Q2, wherein said dairy product is selected from the group consisting of yoghurt, cheese, butter, inoculated sweet milk and liquid fermented milk products.

The invention will now be described in further details in the following non-limiting examples.

EXAMPLES

Example 1: Preparation of Microencapsulated Microbial Culture

Microencapsulation of microbial cultures were prepared as either a coacervation (non-homogeneous) formulation or a homogeneous formulation to evaluate the influence of the encapsulation matrix on subsequent storage stability of the microbial culture.

Methods

The coacervation formulation consisted of *Ligilactobacillus animalis* DSM 33570 incorporated in a non-homogeneous encapsulation matrix consisting of sodium caseinate (3.6%), pectin (1.4%), trehalose (23%), tri-sodium citrate (5%) and water (67%).

Matrix solutions were prepared separately as first (sodium caseinate, trehalose, tri-sodium citrate and water) and second (pectin) matrix solutions. The first and second matrix solutions were heat sterilized, followed by cooling to RT. The *Ligilactobacillus animalis* bacteria culture was mixed with the first matrix solution for 10-15 min at 10° C., followed by mixing with the second matrix solution for 10-15 min at 10° C. The final composition was frozen in liquid nitrogen to form granulates before freeze-drying the granules to obtain freeze dried granulates (FDs).

The homogeneous formulation consisted of *Ligilactobacillus animalis* incorporated in a reference encapsulation matrix consisting of maltodextrin, trehalose dihydrate, tri-sodium citrate dihydrate and water.

A cryo solution containing maltodextrin and trehalose dihydrate in water was prepared. The cryo solution was autoclaved and cooled down to RT, keeping it at refrigerated conditions overnight. Filter sterilized tri-sodium citrate dihydrate was added to the cryo solution and subsequently the *Ligilactobacillus animalis* culture was mixed with the cryo solution for 2 h at less than 10° C. The final mixture was frozen in liquid nitrogen to get pre-freeze dried granulates (PFDs). These PFDs were then freeze dried using safe profile (32° C., 0.3 mbar) to get freeze dried granulates (FDs).

The coacervate formulation and the homogeneous formulation were prepared at ratios (wt %/wt %) of encapsulation matrix to core material of either 1 or 4.

The samples were prepared for probing the storage stability at ambient conditions. Freeze-dried granulates of the coacervation formulation or homogeneous formulation were grinded in a coffee blender for 30 seconds and passed through a #60 mesh (250 μm) sieve. Grinded material was diluted 100 times in calcium carbonate ($CaCO_3$) powder to a final water activity of 0.4 Aw.

Results

The coacervation formulation and the homogeneous formulation comprising *Ligilactobacillus animalis* had comparable and acceptable concentrations (approx. 2E+8 to 5E+8 CFU/g) of active bacteria after 1:100 dilution with calcium carbonate (see FIG. 1).

Conclusions

The present example demonstrates that the coacervation formulation comprising a non-homogeneous encapsulation matrix is suitable for formulating microbial cultures as the number of viable bacteria after preparation is comparable to the homogeneous formulation based on the reference homogeneous encapsulation matrix.

Example 2: Storage Stability of Microencapsulated Microbial Culture

Microencapsulated microbial cultures was investigated to evaluate the effect of the formulation strategy (encapsulation matrix and EI) on culture viability over time when exposed to environmental stress conditions.

The FD powder blend with $CaCO_3$ was packed in Alu bags which were then heat sealed and subjected to storage for extended periods of time.

Methods

The FD powder blend with $CaCO_3$ of Example 1 was packed in aluminium bags which were then heat sealed and subjected to storage stability study at accelerated conditions (temperature=37° C. and Aw=0.4). Samples were withdrawn after 2 and 4 weeks and analysed for CFU/g and Aw. Storage stability was determined as described herein under the definition of storage stability.

Results

Figure 2:
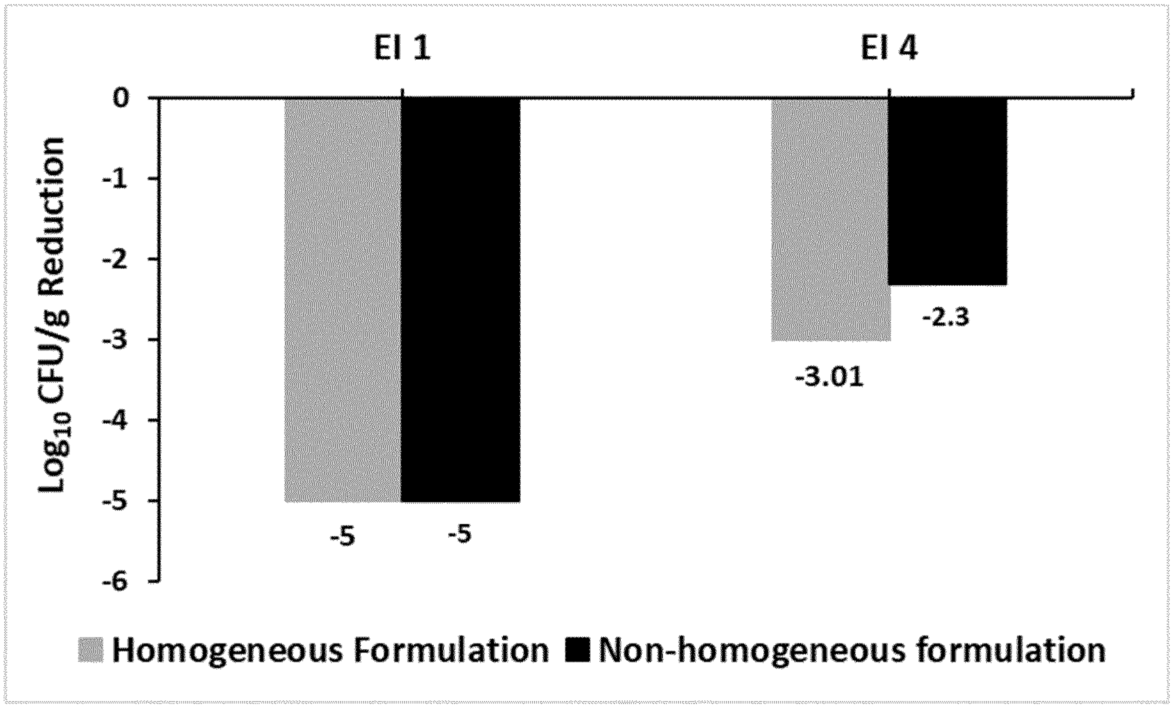
FIG. 2 shows $Log_{10}$ CFU/g reduction for homogeneous and non-homogeneous formulations, respectively, at EI 1 or 4 upon storage for 2 weeks at accelerated conditions of 37° C. and 0.4 Aw.

The results clearly show that at EI=1, neither the non-homogeneous coacervate formulation nor the homogeneous formulation provided any stability at accelerated storage conditions, with more than 5 log units reduction in CFU/g after 2 weeks. In contrast, when the EI was increased to 4, the homogeneous formulation showed a reduction of CFU/g of 3 log units and the non-homogeneous coacervation formulation showed a reduction in CFU/g of only 2.3 log units, providing much enhanced protection compared to EI 1 (see FIG. 2).

Figure 3:
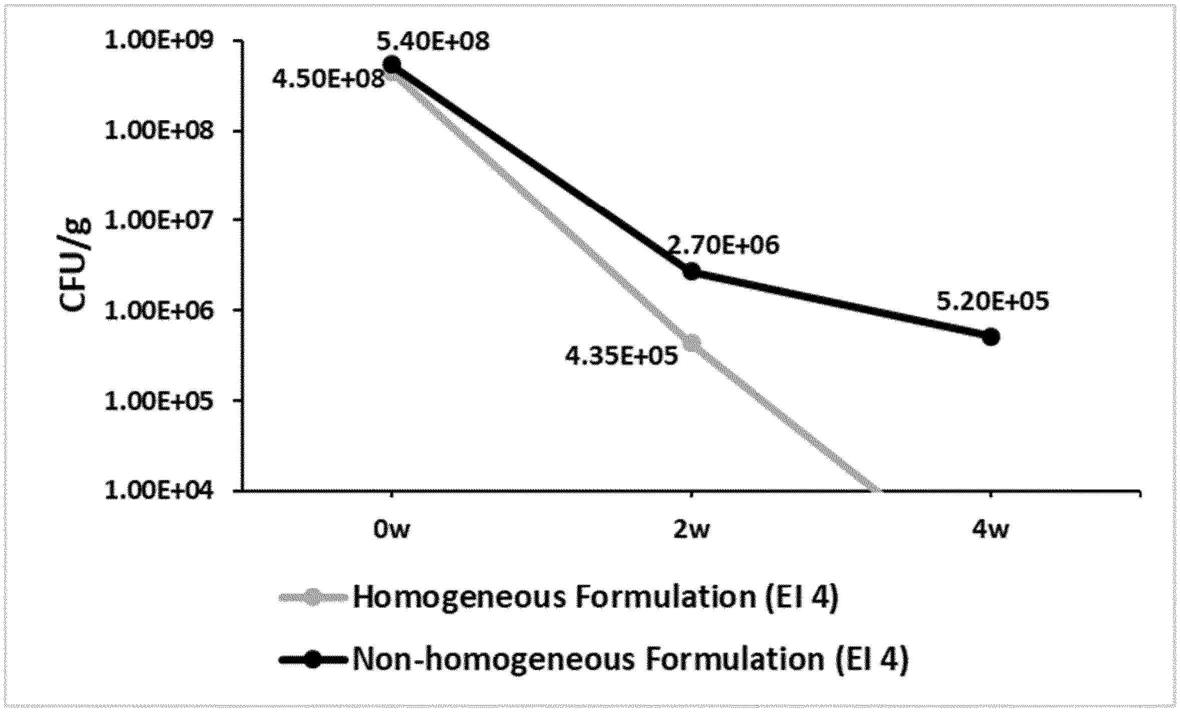
FIG. 3 shows the absolute CFU/g counts for homogeneous and non-homogeneous formulations, respectively, at EI 4 upon storage for up to 4 weeks at accelerated conditions of 37° C. and 0.4 Aw.

The protective effect of the non-homogeneous coacervate formulation was even more pronounced when the absolute CFU/g counts were compared after 4 weeks of storage at accelerated storage conditions. After 4 weeks, the homogeneous formulation did not provide any further protective effect and the count of viable bacteria was below the detection limit. However, the coacervate formulation provided extended storage stability and still possessed a significant number of viable bacteria after 4 weeks of storage (see FIG. 3).

Conclusion

This experiment demonstrates that the combination of a non-homogeneous encapsulation matrix and high EI yields a protective microencapsulation that increases stability of microbial cultures stored under accelerated storage conditions.

REFERENCES

Seifert & Mogensen (2002), Bulletin of the IDF, 377, 10-19

Zheng et al. (2020), Int. J. Syst. Evol. Microbiol., 70, 2782-2858

The invention claimed is:

1. A microencapsulated microbial culture, wherein said microbial culture is entrapped in a coacervate comprising:

i) a core material comprising a microbial culture, and ii) an encapsulation matrix comprising one or more matrix components;

wherein the ratio (wt %/wt %) of encapsulation matrix to core material is at least 2;

wherein the encapsulation matrix is a non-homogenous matrix;

wherein the encapsulation matrix comprises at least two matrix components; and wherein the first matrix component comprises sodium caseinate, trehalose and trisodium citrate and the second matrix component comprises pectin.

2. The microencapsulated microbial culture according to claim 1, wherein the microbial culture is a bacterium or a yeast.

3. The microencapsulated microbial culture according to claim 1, wherein the microbial culture is a probiotic culture.

4. The microencapsulated microbial culture according to claim 1, wherein, after storage for 2 weeks at 37° C. at a water activity (Aw)≤0.4, the microbial culture exhibits a loss in viability as measured by CFU/g of less than 3 log units.

5. A composition comprising the microencapsulated microbial culture according to claim 1.

6. The composition according to claim 5, wherein the composition further comprises one or more additives selected from the group consisting of food-grade ingredients, feed-grade ingredients, pharmaceutical ingredients and excipients.

7. A product comprising the microencapsulated microbial culture according to claim 1, wherein the product is selected from the group consisting of a feed, a plant health product, a food, a beverage and a pharmaceutical product.

8. A method for preparing a microencapsulated microbial culture according to claim 1, comprising the steps of:

(i) mixing a microbial culture with a first matrix comprising one or more first matrix components to form a first mixture, and (ii) mixing the first mixture with a second matrix comprising one or more second matrix components to form a microencapsulated microbial culture, wherein said one or more first matrix components and said one or more second matrix components are not the same.

9. A microencapsulated microbial culture obtained by a method according to claim 8.

10. The microencapsulated microbial culture according to claim 1, wherein the ratio (wt %/wt %) of encapsulation matrix to microbial culture is at least 2.

11. The microencapsulated microbial culture according to claim 1, wherein the core material consists of the microbial culture.

12. The microencapsulated microbial culture according to claim 1, wherein the microbial culture comprises lactic acid bacteria.

* * * * *